United States Patent [19]
Rödel et al.

[11] 3,937,581
[45] Feb. 10, 1976

[54] ANALYTIC CELL FOR USE IN HIGH-SPEED ULTRA CENTRIFUGES

[75] Inventors: Egon Rödel, Osterode; Volker Neuhoff, Goettingen, both of Germany

[73] Assignees: Heraeus-Christ GmbH, Osterode, Harz; Max-Planck-Gesellschaft zur Foerderung der Wissenschaften e.V., Goettingen, both of Germany

[22] Filed: May 13, 1974

[21] Appl. No.: 469,539

[30] Foreign Application Priority Data
May 17, 1973 Germany............................ 2324879

[52] U.S. Cl. ................... 356/246; 233/26; 356/197
[51] Int. Cl.² ......................................... G01N 1/10
[58] Field of Search ............... 356/197, 246; 233/26

[56] References Cited
UNITED STATES PATENTS
3,391,597  7/1968  Gropper...................... 356/197 UX
3,778,171  12/1973  Chervenka...................... 356/197 X

*Primary Examiner*—James B. Mullins
*Attorney, Agent, or Firm*—Flynn & Frishauf

[57] ABSTRACT

A housing retains an essentially disk-like center element made of light-transmissive material, or formed with an opening therein, and shaped to receive a capillary tube (or formed with a capillary opening itself) extending radially transversely to the disk-shaped element, essentially half-way in the thickness thereof, the central element being bounded on at least one side by window-like diaphragm elements, either separate parts or incorporated on the central part to define a light path through the capillary tube to permit centrifuging and optical investigation of minute quantities of substances to be tested by centrifuging, for example blood sera to determine sedimentation.

19 Claims, 16 Drawing Figures

ANALYTIC CELL FOR USE IN HIGH-SPEED ULTRA CENTRIFUGES

The present invention relates to an analytical cell to be combined or built into the rotor of an ultra high-speed centrifuge, and more particularly to a cell structure into which a test vessel is to be inserted, to contain a substance which is to be optically evaluated during centrifuging.

Cells to be assembled in centrifuges have previously been proposed — see, for example, Canadian Pat. No. 771,511. The cells are mounted on the rotor of a centrifuge which may revolve at a speed of 60,000 or more rpm. The cells must be liquid-tight and must not deform even when being subjected to the substantial centrifugal forces arising due to the high rotational speed. The construction of such cells is therefore complicated.

It was usually necessary to provide cells having a sector-shaped free space having a volume of about 1 ml. To examine a substance in a solution present in for example, 0.1%, a quantity of about 1 mg of sample is necessary. This is a very small amount; for some investigations, particularly in the biochemical field, it is still much too high, however; for example, for some neurochemical investigations, quantities of samples of $10^{-5}$g or less are sometimes all that is available. Such extremely small quantities have already been examined by use of thin glass capillaries in suitable rotors in preparatory centrifuging (see, for example, G I T - Fachzeitschrift fur das Laboratorium, Vol. 13, Issue 2, February 1969, pp. 86a–87; translated as: "Journal for Laboratories"). Preparatory centrifuging of test samples of substances only permits evaluation of concentration, and thus quantity of the substance.

It is an object of the present invention to provide a device which permits determination of the sedimentation coefficient using minute quantities of test substance, besides permitting quantitative as well as qualitative investigation of the test sample.

Subject matter of the present invention

Briefly, the rotor of an ultra high-speed centrifuge is shaped to receive a measuring or test cell therein which is so constructed that it has a central element which is formed with an opening within which a capillary can be received. The capillary is made of a light-transmissive substance. The opening includes a longitudinal slit, the capillary extending throughout the length of the longitudinal slit.

The cell, in accordance with the present invention, permits use of sampling volumes which are less than the sampling volumes of the customary analytical cells by a factor of about a thousand. Thus, while customary cells require about 1 cm³ volume, the cells of the present invention can be used to analyze quantities of $10^{-3}$ cm³.

An analytic ultra centrifuge which is arranged for absorption measuring, and using a customary analytic monosector cell can be used to determine, for example, layer sedimentation of nucleic acids at a concentration of $C_1$. Assuming a volume $V_1$ of about 1cm³, a 12 mm thickness $(d_1)$ layer, the limit of resolution at band forming sedimentation of the above referred to nucleic acid will be in the order of $5 \cdot 10^{-3}$ ppm $= 5 \cdot 10^{-9}$g $\cdot$ cm$^{-3}$. Using a capillary with an internal diameter $(d_2)$ of about 0.2 mm, the corresponding concentration at the same extinction value $E$ can be calculated according to the Lambert-Beer relationship, corresponding to the relevant thickness layer, as set forth in relationship (1). Substituting values results in relationship (2). The fill volume $V_2$ of a microcapillary of 10 mm length and an internal diameter of 0.2 mm is set forth in relationship (3). The quantity $(m_2)$ within the capillary will then be as set forth in relationship (4).

The example above given shows the absolute limit of determination, based on the foregoing assumptions; this limit of determination of course depends on the extinction coefficient of the test sample substance.

RELATIONSHIPS:

$$E = \epsilon \cdot d_1 \cdot c_1 = \epsilon \cdot d_2 \cdot c_2$$

$$\frac{c_1}{c_2} = \frac{d_2}{d_1}$$

$$c_2 = c_1 \frac{d_1}{d_2} \tag{1}$$

$$c_2 = 5 \cdot 10^{-9} \cdot \frac{12}{0.2} = 3 \cdot 10^{-7} \, gcm^{-3} \tag{2}$$

$$r^2 \cdot \pi \cdot h = 0.01 \cdot 3.14 \cdot 10 = 0.3 \cdot 10^{-3} \, cm^3 \tag{3}$$

$$c_2 = \frac{m_2}{V_2}, \; m_2 = c_2 \cdot V_2 = 3 \cdot 10^{-7} \cdot 0.3 \cdot 10^{-3} = 1 \cdot 10^{-10} g \tag{4}$$

$$\frac{5 \cdot 10^{-9}}{1 \cdot 10^{-10}} = 50 \tag{5}$$

Comparing the foregoing with a previously known, customary analytical cell of 12 mm thickness, in which the value for the resolution limit is $5 \cdot 10^{-9}$, an improvement by a factor of 50 can be expected by using the present invention, as can be demonstrated by relationship (5).

It is a substantial advantage with respect to customary analytical cells that the test or sample material in the cell of the present invention remains from the start of the test to its end in a completely closed vessel, that is, the capillary. Losses in substance which otherwise arise when samples are filled and re-filled are thus reliably avoided. A capillary tube, which is closed, and filled with the substance is inserted into the analytical cell. The advantage of retaining the entire substance to be tested in a capillary is particularly important when the substance is dangerous, or difficult to handle, for example when using samples with radioactive traces, or samples which are infectuous, such as infected blood sera, highly infectious virus cultures, or the like, to be centrifuged and analyzed. In such cases, contamination of the entire analysis system can easily occur when using previously customary analysis techniques. Disposal or decontamination of analytic cells thus can be extremely costly; disposal of a capillary is inexpensive. The advantage of the arrangement in accordance with the present invention is particularly marked if expensive substances are to be analyzed, that is, substances which may involve preparation costs of thousands of dollars and extensive time of highly skilled personnel. The necessary test volume to carry out centrifugal analysis in the cell of the present invention can be as low as about 1 microliter; requiring only such a small quantity of test substance is a further advantage of the present invention.

After centrifuging, the capillary vessel, in accordance with the present invention, can be removed, without damage, from the cell and the sample therein contained can be subjected to other analytical methods or tests, or can be removed, without any loss, by means of a capillary pipette.

The invention will be described by way of example with reference to the accompanying drawings, wherein.

Figure 3:
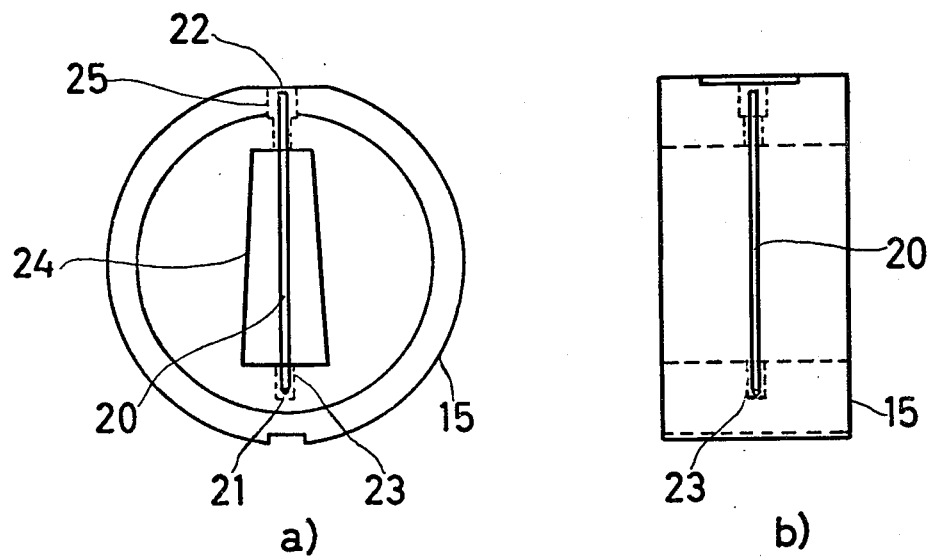

FIG. 3 in views a, b, respectively, shows an analytic cell in which

FIG. 3, view a, is a top view, and

Figure 4:
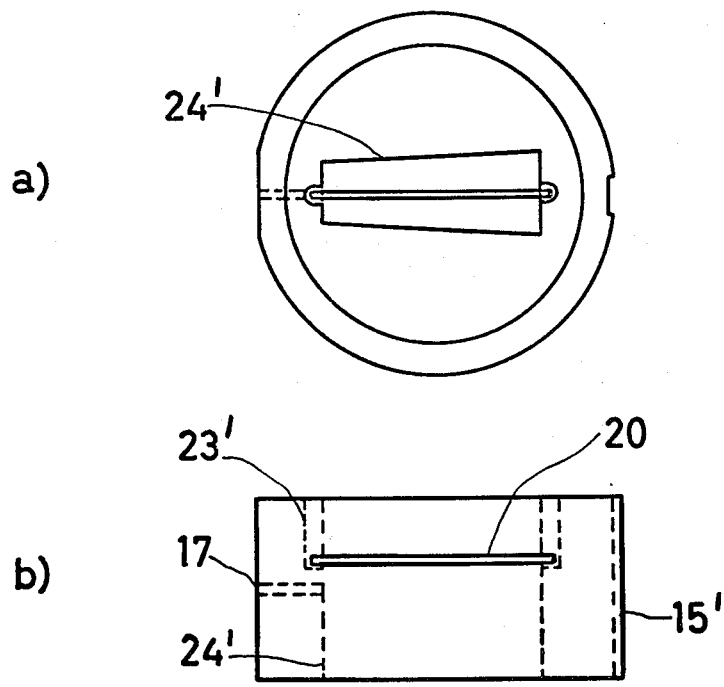
Figure 5:
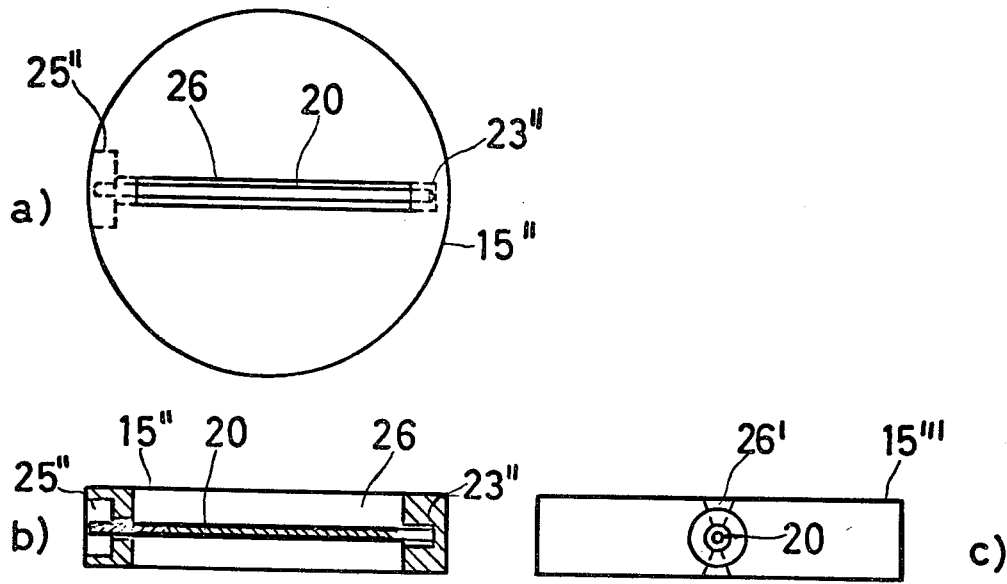
Figure 6:
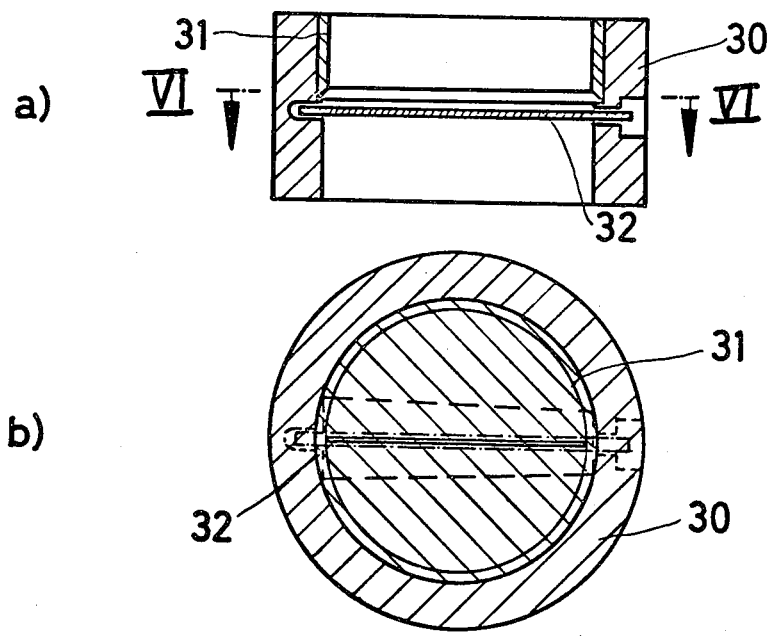

FIG. 3, view b, is a side view of the cell;

FIG. 4, collectively, is another embodiment of the cell of the present invention in which FIG. 4, view a, is a top view, and FIG. 4, view b, is a side view;

FIG. 5 illustrates another embodiment of the cell of the present invention in which FIG. 5, view a, is a top view, FIG. 5, view b, is a vertical section, and FIG. 5, view c, is a side view;

FIG. 6 illustrates yet another embodiment of the cell in which

FIG. 6, view a, is a longitudinal section, and

Figure 7:
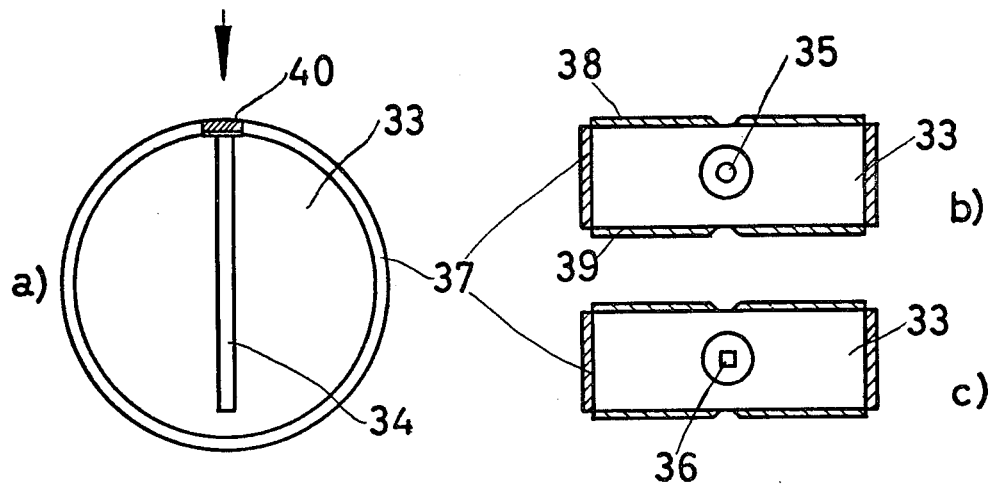

FIG. 6, view b, is a transverse section taken along line VI—VI of view a;

FIG. 7 shows another embodiment of the cell in which

FIG. 7, view a, is a top view,

FIG. 7, view b, is a side view, and

Figure 8:
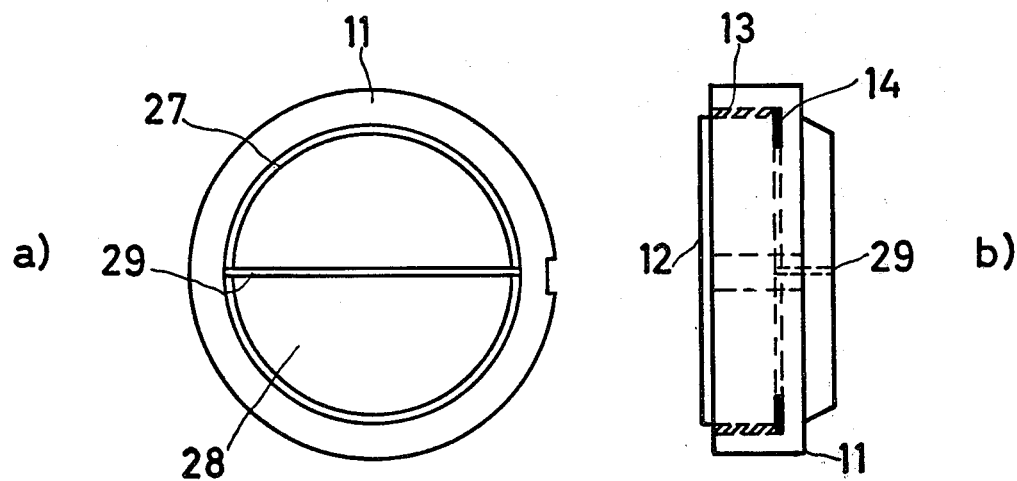

FIG. 7, view c, is a side view illustrating a modification of the arrangement shown in FIG. 7, views a and b; and FIG. 8 illustrates a socket for a window of the cell, for example for the embodiments of FIGS. 3 and 4 in which FIG. 8, view a, is a top view, and FIG. 8, view b, is a side view, partly in section.

Figure 1:
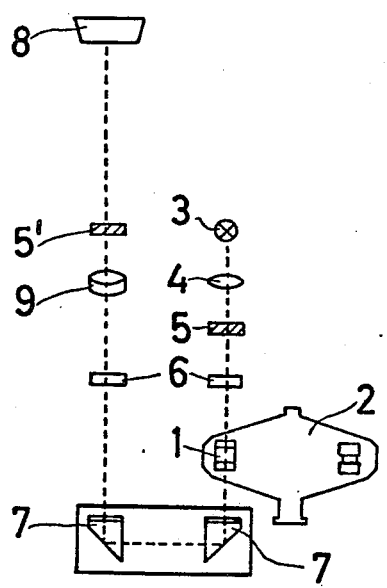
FIG. 1 is a schematic general overall view of a rotor of an ultra centrifuge in which the cell according to the present invention is assembled.

The cell 1 (FIG. 1) is mounted in the rotor of an analytic ultra centrifuge. Upon operation, the centrifuge may rotate at a speed which can reach 60,000 rpm, or more, to permit qualitative investigation of samples in the centrifuge. The samples can be optically evaluated, particularly to determine sedimentation. Test runs can be carried out which may extend over various hours. Optical investigation of the samples in the centrifuge can be carried out, for example, by utilizing a light source 3 from which a beam of light, indicated by dashed lines in FIG. 1, is directed through a collimator lens 4, then at least through one filter 5, a window 6, and then through the sample. A reflecting system, such as mirrors or prisms 7, reflects the light through the sample which is then passed through another window, through the objective lens 9 of a camera 8, with or without the interposition of another filter 5'. The light passing through the test sample may also be electronically evaluated by suitable electronic apparatus, rather than in a camera.

Tests for sedimentation of about 1 mm$^3$ of 1% hemoglobin solution, utilizing the cell according to the present invention, were successful. The absolute quantity of the test substance was only $10^{-5}$g. Optical evaluation was carried out by using monochromatic interference filters, with a light wave length of 407 nm. The system of moving boundary sedimentation was used in the tests with the cell according to the present invention. By use of the method which is termed band forming by overlayering or equilibrium run, in which the substance is concentrated in small zones, an even smaller quantity of test substance than the sample of $10^{-5}$ g could be analyzed by use of optical evaluation upon centrifuging. The capillaries used in the analytical cells in accordance with the present invention are excellently suited for concentration of the test substance in accordance with the band forming technique; the test substance within the capillary remains collected therein and may be utilized again after centrifuging for other investigations. The capillary can be introduced, and removed from the analytic cell by simple tools, as will be apparent as the description proceeds.

The analytical cell for use in the centrifuge of FIG. 1 generally includes a cell housing 10 (FIG. 2), a window socket 11, windows 12, spacer inserts 13, and washers 14. The heart of the cell itself is a center holder element 15. The center holder element 15 is formed with an opening or hollow space 16 which is generally sector-shaped, and further with an introduction opening 17 into which the sample capillary can be inserted. The insertion or introduction opening 17 is closed off by a terminal screw 18, for tight closing thereof. The components of the cell are inserted into the housing 10 and held in fixed, aligned relationship by an end thread ring 19. The housing 10, as well as the cell elements having outer circumferential surfaces are formed with mating non-circular surfaces to prevent relative rotation, such as a ridge and mating groove formed on the parts, a flattened surface, the parts being so arranged that the end ring 19 can still be screwed into housing 10. The center element 15 may be made of metal, for example titanium, or a light-weight metal such as aluminum; or it can be made of plastic, for example an epoxy resin.

The capillary, into which the test sample is introduced is located in the center element 15, as clearly appears from FIG. 3. The capillary tube 20 is introduced from an open side into a blind bore 23. The closed end 21 of the capillary is located at the blind end of the bore 23, the open end 22 of the capillary 20 being located at the other end of the bore. The size and shape of the bore 23 is so selected that the axis of the bore 23 coincides with the longitudinal axis of the sector-shaped slit 24, looked at in direction of the top side of the center element — FIG. 3, view a. The bore 23 is enlarged at its free end, as seen at 25, to facilitate insertion of the capillary 20. As seen in FIG. 3, the center element 15 is a unitary center element. The invention is not limited to single elements in which a single slit or opening is placed, or in which only a single capillary is located. The center element, together with the covering windows (preferably quartz) form a sort of cuvette, located in the optical path as seen in FIG. 1.

FIG. 4 illustrates another example of a center element into which the capillary 20 can be inserted from above. The center element 15' is formed with an opening 23', which is slit-shaped, and located at the two ends of a center-shaped gap 24'. The openings 23', in slit shape, are located in alignment with the central axis of the sector-shaped slit 24'. The opening or slit 23' extends roughly to half the thickness of the center element 15'. Capillary 20 is dropped in from the top, rather than being inserted laterally (as in FIG. 3). A suitable holding clip (not shown) can be used to locate the capillary 20 in position in the centrifuge center element 15'.

The center element 15'' of FIG. 5 has a radially extending rectangular slit 26, which is extended radially by extensions 23'' to form a bore similar to bore 23 (FIG. 3). The bore 23'' is, preferably, likewise formed as a blind bore, as indicated at the right-hand side thereof in FIG. 5. The rectangular slit 26, at the center thereof, is just slightly wider than the outer diameter of capillary 20. It may have the same width at the surface of the center element 15''. Capillary 20 is radially introduced from the outside into the inner portion of center element 15'', so that its closed end is placed in the blind bore end of bore 23''. As seen in FIG. 5, view c, the center element 15''' may be formed with divergent radial slits 26, which are essentially V-shaped in cross section. This form of slit 26 permits better utilization of light energy from the light source, and provides for convergent illumination of the capillary 20. Slit 23''' is enlarged at its free end, as seen at 25'' to facilitate insertion of capillary 20.

The center element may be formed differently, as seen in FIG. 6, in which an essentially ring-shaped body 30, of metal or plastic, is provided to retain the capillary 32. A pot or cup-shaped insert 31, likewise of metal or plastic, is formed with a slit having a diameter which is equal to or smaller than the inner diameter of capillary 32. The insert is so placed that the slit is just above the capillary 32. Capillary 32, itself, is inserted into the housing 30 similarly to the insertion described in connection with FIG. 3. The embodiment of FIG. 6 has the advantage that stray interfering light which can pass the interior of the capillary at the right and at the left thereof can be readily shaded off, thus providing for improved quality of the optical imaging of the capillary.

Figure 2:
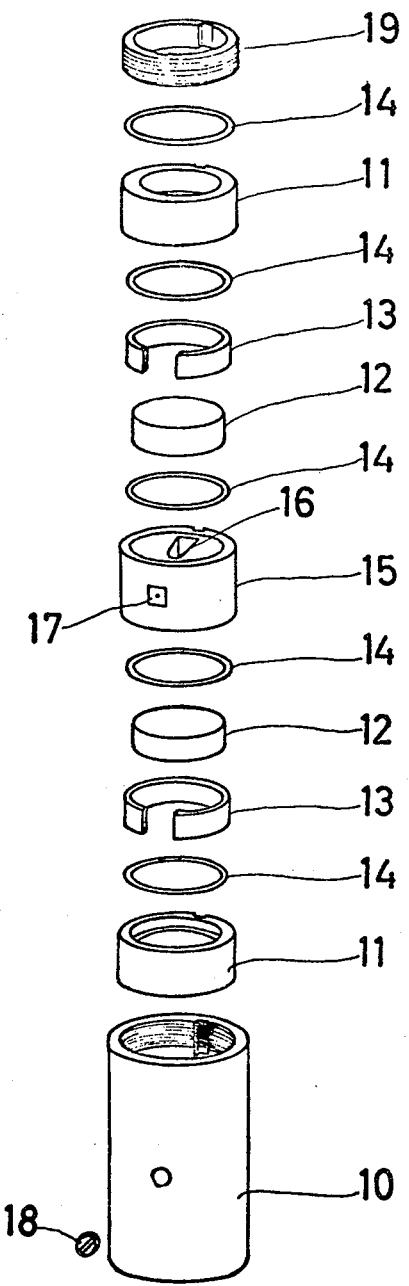
FIG. 2 is an exploded view of the analytical cell of the present invention, to be assembled in the rotor of FIG. 1.

Embodiment of FIG. 7: A quartz disk 33, having the upper and lower surfaces accurately ground to be parallel, has a capillary bore 34 formed therein, extending radially inwardly. The bore 34 may have a circular cross section, as seen in FIG. 7, view b, at 35; or it may have a different cross section, for example square, as seen in view c, at 36. The quartz disk itself may be secured in a socket or ring 37 which is made of a suitable material such as metal or plastic, to provide for ready adaptation of the outside diameter of the quartz disk 33 to the interior dimension of the housing or holder 10 (FIG. 2). This ring or sleeve or socket 37 may be metal or a suitable plastic, which may, simultaneously, be formed with a closure 40 which, for example, may be a screw with vacuum closure. This embodiment has the additional advantage that a liquid of the same density or, respectively, the same index of refraction, as the glass of the capillary tube, and surrounding the capillary tube in bore 34 need not be used; further, stray light masks 38, 39 (views b and c) may be formed directly on the quartz disk, for example as a surface layer which is vapor-deposited on the surfaces of the quartz disk. The quartz disk, thus, can be made simpler, and eliminates some of the components such as windows, spacer rings and the like used in the assembly illustrated in FIG. 2.

The center element of the analytical cells in accordance with FIG. 5, or with FIG. 7, can be made axially shorter than the cells of the other embodiments, or of the prior art; this decrease in axial length can be carried out to such an extent that the cell is only one quarter to one third of the thickness of previously known cells. Decreasing the thickness (that is, the axial dimension) of the cells has the advantage that disk rotors can be used in the centrifuge; disk rotors have higher stability and strength, and the centrifuge can therefore be operated at higher speed. Such disk rotors further have a lower mass, so that the rotor will accelerate more rapidly with lower energy consumption, and lower structural strength requirements being placed on the centrifuge itself.

FIG. 8 illustrates the socket of a window which can be placed adjacent the center element of the cell in accordance with the present invention, preferably being located immediately adjacent the center element of the cell itself. Window 12 (FIG. 2) is located in a socket 11 by means of an intermediate washer 14 and an insert sleeve or spacer 13. The socket 11 is so constructed that it forms two, roughly semicircular diaphragms 27, 28 which, between themselves, define a slit 29 having a width corresponding approximately to the outer diameter of the capillary 20. The window essentially eliminates the influence of stray light.

The cells of FIGS. 5 – 7 have the following additional advantages. Capillary 20, or the cell of FIG. 7 itself is transparent, and therefore a separate window can be eliminated. In accordance with FIG. 5, the capillary 20 can be introduced into the center of the cell element 15'' by means of an auxiliary tool, such as by forceps, tweezers, or plier-like holders, which may during insertion of the capillary bear against the enlarged end 25'' of opening 23'' (FIG. 5). After introduction of the capillary 20, the cell is closed by means of a sealing plug, or a screw. The cell, in accordance with FIG. 7, can be inserted without further additional fittings or windows into the rotor of the centrifuge.

When using the cells of the examples of FIGS. 3, 4 and 6, the interior of the cell 24 can be filled with a suitable liquid to such an extent that capillary 20 is completely surrounded by the liquid. This prevent rupture of the capillary 20, if it should have low wall thickness, due to the centrifugal forces arising during rotation of the centrifuge. Further, distortion due to any uneven surfaces of the capillary, which may interfere with optical evaluation of the contents, is thereby effectively avoided. The liquid should be so selected that the index of refraction of the liquid corresponds to that of the material of which the capillary is made; for quartz glass, for example, $n_D = 1.458$. The center portion of the embodiment of FIG. 5 may, of course, also be filled with a similar liquid.

Various changes and modifications may be made within the scope of the inventive concept and features described in connection with any embodiment may, suitably, be applied to any other embodiment.

We claim:

1. Analytic cell for use in a centrifuge, particularly an ultra high-speed centrifuge comprising
    a housing (10);
    a disk-shaped central part (15, 30) located in the housing and formed with a radially extending light-transmissive slit across the part (24, 24', 26, 26', 29), the central part being further formed with a radially extending opening extending in alignment with the light-transmissive slit and of sufficient size to permit introduction of a capillary tube therein;
    and a capillary tube of light-transmissive material located in said opening and for optical evaluation of test substances within the capillary tube located in alignment with said slit.

2. Cell according to claim 1, wherein (FIG. 3) the central part is essentially disk-shaped and the opening (23) is a blind bore extending from the outside surface essentially radially inwardly.

3. Cell according to claim 1, wherein the central part (15') is essentially disk-shaped and the opening (23') is in the form of notches extending from an end surface approximately half the thickness of the disk-shaped central part.

4. Cell according to claim 1, wherein the central part is of metal.

5. Cell according to claim 1, wherein the light-transmissive slit is formed as a sector-shaped opening (FIG. 3: 24) extending axially through the central part.

6. Cell according to claim 1, wherein the light-transmissive slit comprises an essentially rectangular opening (FIG. 5: 26).

7. Cell according to claim 1, wherein the center element is essentially disk-shaped and the light-transmissive slit comprises a transverse opening (FIG. 5, view c: 26') having divergent sides, the opening (23") retaining the capillary being located at the point of convergence of the divergent sides.

8. Cell according to claim 1, wherein (FIGS. 2, 8) the central part comprises a composite assembly including a disk-like element (15) formed with said opening to receive the capillary tube, and a masking or diaphragm part (31) defining said slit (29) and located adjacent the disk-like element (30).

9. Cell according to claim 8, wherein the width of the slit (29) is equal to or less than the inner diameter of the capillary (20) and is located immediately adjacent the capillary.

10. Cell according to claim 1, further comprising window elements located at opposite sides of said central part;
and a liquid having similar density or index of refraction as the capillary tube surrounding the capillary tube and located between said disks.

11. Cell according to claim 1, further comprising window elements (12); socket means (11) retaining the window elements (12) immediately adjacent the central part, the radially extending light-transmissive slit being formed by a diaphragm means.

12. Cell according to claim 1, wherein the radially extending slit has a width which is equal to or less than the inner diameter of the capillary tube.

13. Cell according to claim 12, wherein a sleeve or socket (37) is provided surrounding said quartz disk (33), the sleeve or socket being formed with a closure (40) to close the bore (34) and being adapted to fit in said housing (10).

14. Cell according to claim 1, wherein the central part comprises a quartz disk (FIG. 7: 33) having a capillary bore (34) formed therein to receive the capillary tube holding the test substance.

15. Cell according to claim 14, wherein the bore (34) in the quartz disk (33) to receive the capillary tube has circular cross section.

16. Cell according to claim 14, wherein the bore (34) in the quartz disk (33) to receive the capillary tube has square cross section.

17. Cell according to claim 14, wherein (FIG. 7) at least one of the end surfaces of the quartz disk (33) has a layer of opaque diaphragm means (38, 39) applied thereto, said diaphragm means being formed to leave said radially extending light-transmissive slit (29) in alignment with said bore (34), the width of said diaphragm slit (29) being equal, or less than the width of said bore (34).

18. Cell according to claim 1, wherein the central part (FIG. 7: 33) comprises a disk of transparent material, and said opening is of such size to receive said capillary tube, extending radially into the disk from an outside surface thereof, approximately centrally of the width thereof.

19. Cell according to claim 1, wherein the central part is of plastic.

* * * * *